(12) United States Patent
Park et al.

(10) Patent No.: US 11,890,091 B1
(45) Date of Patent: Feb. 6, 2024

(54) METHOD OF PROVIDING WHETHER PATIENT IS ACCOMPANIED BY CAREGIVER AND DEVICE USING THE SAME

(71) Applicants: INDUSTRY-ACADEMIC COOPERATION FOUNDATION, YONSEI UNIVERSITY, Seoul (KR); PEOPLE & TECHNOLOGY INC., Seoul (KR)

(72) Inventors: Jin Young Park, Seoul (KR); Duk Yong Yoon, Suwon-si (KR); Soo Jeong Kim, Yongin-si (KR); Dong Won Kim, Anyang-si (KR); Ji Hoon Seo, Gwangmyeong-si (KR); Woo Chul Jung, Seoul (KR)

(73) Assignees: INDUSTRY-ACADEMIC COOPERATION FOUNDATION, YONSEI UNIVERSITY, Seoul (KR); PEOPLE & TECHNOLOGY INC., Seoul (KR)

(*) Notice: Subject to any disclaimer, the term of this patent is extended or adjusted under 35 U.S.C. 154(b) by 0 days.

(21) Appl. No.: 18/239,749

(22) Filed: Aug. 29, 2023

(30) Foreign Application Priority Data

Apr. 13, 2023 (KR) .................. 10-2023-0049003

(51) Int. Cl.
*G08B 21/02* (2006.01)
*A61B 5/11* (2006.01)
(Continued)

(52) U.S. Cl.
CPC .......... *A61B 5/1113* (2013.01); *A61B 5/7275* (2013.01); *A61B 5/746* (2013.01); *G16H 40/20* (2018.01); *G16H 40/67* (2018.01)

(58) Field of Classification Search
USPC ....... 340/573.1, 539.12, 539.1, 572.1, 573.4, 340/539.13
See application file for complete search history.

(56) References Cited

U.S. PATENT DOCUMENTS

2005/0035862 A1* 2/2005 Wildman ........... G08B 13/2462
340/572.1
2008/0015903 A1* 1/2008 Rodgers ................. G06Q 30/02
705/3
(Continued)

FOREIGN PATENT DOCUMENTS

| KR | 10-2013-0092763 A | 8/2013 |
| KR | 10-1540330 B1 | 7/2015 |
| KR | 10-2020-0119928 A | 10/2020 |

*Primary Examiner* — Daniel Previl
(74) *Attorney, Agent, or Firm* — INVENSTONE PATENT, LLC

(57) ABSTRACT

The present disclosure relates to a method for providing whether a patient is accompanied by a caregiver and a device using the same, the method for providing whether the patient is accompanied by the caregiver being configured to be implemented by a processor and including receiving an outpatient clinic record from a user device, tokenizing each sentence of the outpatient clinic record as a unit of at least one token, encoding the tokenized outpatient clinic record as an integer, and determining whether a psychiatric symptom occurs for a patient related to the outpatient clinic record by inputting the encoded outpatient clinic record by using a determination model that uses the encoded outpatient clinic record as an input and uses whether the psychiatric symptom occurs as an output.

16 Claims, 11 Drawing Sheets

(51) Int. Cl.
  *G16H 40/20* (2018.01)
  *A61B 5/00* (2006.01)
  *G16H 40/67* (2018.01)

(56) References Cited

U.S. PATENT DOCUMENTS

| | | | |
|---|---|---|---|
| 2011/0093296 A1* | 4/2011 | Klink .................... | G16H 10/65 |
| | | | 705/3 |
| 2014/0298586 A1* | 10/2014 | Van Thienen ......... | A47C 21/00 |
| | | | 5/500 |
| 2014/0340227 A1* | 11/2014 | Reed, Jr. ................ | G08B 21/02 |
| | | | 340/573.1 |
| 2014/0368335 A1* | 12/2014 | Jordan ................. | G08B 25/016 |
| | | | 340/539.13 |
| 2015/0109442 A1* | 4/2015 | Derenne ................ | H04N 7/185 |
| | | | 348/143 |
| 2018/0211724 A1* | 7/2018 | Wang ..................... | G16H 40/20 |
| 2021/0158965 A1* | 5/2021 | Receveur ............... | G16H 50/20 |
| 2021/0338178 A1* | 11/2021 | Essex .................... | A47K 13/00 |

* cited by examiner (a) | GIL-DONG HONG | H1 | TARGET | HIGH RISK | - | DEV000001 |

(b) | FALL RISK ZONE 1 | A1 | P1(X1,Y1),P2(X1,Y2), ...PN(XN,YX) | Y (DANGEROUS) | WHOLE DAY |

(c) | GIL-DONG HONG | H1 | FALL RISK ZONE 1 | A1 | DANGEROUS SITUATION = Y |

(d) | GAN-BYEONG KIM | C1 | CAREGIVER | H1 | DEV000002 |

|   |   | S | E | L | E | C | T |
|---|---|---|---|---|---|---|---|
|   | 0 | 1 | 2 | 3 | 4 | 5 | 6 |
| S | 1 | 0 | 1 | 2 | 3 | 4 | 5 |
| E | 2 | 1 | 0 | 1 | 2 | 3 | 4 |
| L | 3 | 2 | 1 | 0 | 1 | 2 | 3 |
| E | 4 | 3 | 2 | 1 | 0 | 1 | 2 |
| C | 5 | 4 | 3 | 2 | 1 | 0 | 1 |
| T | 6 | 5 | 4 | 3 | 2 | 1 | 0 |
| I | 7 | 6 | 5 | 4 | 3 | 2 | 1 |
| O | 8 | 7 | 6 | 5 | 4 | 3 | 2 |
| N | 9 | 8 | 7 | 6 | 5 | 4 | ③ |

SELECT ↕ SELECTION

1102

(a)

<Levenshtein distance percentile>

$$\frac{\text{length of longer string} - \text{levenshtein distance}}{\text{length of longer string}} \times 100$$

(b)

| GIL-DONG HONG | H1 | FALL RISK ZONE 1 | A1 | LONE WANDERING = Y |
|---|---|---|---|---|

METHOD OF PROVIDING WHETHER PATIENT IS ACCOMPANIED BY CAREGIVER AND DEVICE USING THE SAME

CROSS-REFERENCE TO RELATED APPLICATIONS

This application claims the priority of Korean Patent Application No. 10-2023-0049003 filed on Apr. 13, 2023 in the Korean Intellectual Property Office, the disclosure of which is incorporated herein by reference.

BACKGROUND

Field

The present disclosure relates to a method of providing whether a patient is accompanied by a caregiver and a device using the same.

Description of the Related Art

A system for managing the safety of hospitalized patients calculates a value of a risk degree, in respect to a safety accident such as a fall accident during a patient visit, and allows medical staff to conduct a periodic visit and check a dangerous time or the like. Alternatively, the system may track positions of a patient and a caregiver, monitor a position of the patient positioned outside a hospital room on the basis of position information, and generate a notification when the patient enters or exits a dangerous zone.

In this case, in case that the medical staff conducts a periodic visit, there may occur a problem in that a blind spot occurs in accordance with a time zone. Further, in case that an alarm is generated when the patient enters or exits the dangerous zone, there occurs a problem in that whether the patient is accompanied by a caregiver cannot be determined, and a person needs to separately identify whether the patient is accompanied by the caregiver.

The Background Art is provided to make it easy to understand the present disclosure. It should not be interpreted that the contents disclosed in the Background Art are present in prior arts.

Summary

Meanwhile, the inventors related to the present disclosure have performed a method of identifying whether the patient is accompanied by the caregiver by tracking positions by simply calculating a distance between the patient and the caregiver. In case that whether the patient is accompanied by the caregiver is determined by simply calculating the distance, there may occur a time difference when position data of the patient and the caregiver are collected. As described above, an error occurs because of the time difference made when the position data of the patient and the caregiver are collected, and the error may cause a problem in that the precision of the process of identifying whether the patient is accompanied by the caregiver is degraded.

In order to solve the above-mentioned problems, the inventors related to the present disclosure intended to develop a method of providing whether a patient is accompanied by a caregiver in a highly accurate manner.

As a result, the inventors related to the present disclosure a method and a device using the same, which determine whether a patient is accompanied by a caregiver on the basis of a method of setting a dangerous zone and a dangerous time in a hospital and minimizing an error caused by a time difference made when position data of the patient and the caregiver are collected when the patient wanders in the dangerous zone or at the dangerous time, and the method and device being capable of raising an alarm when the patient is not accompanied by the caregiver.

Technical problems of the present disclosure are not limited to the aforementioned technical problems, and other technical problems, which are not mentioned above, may be clearly understood by those skilled in the art from the following descriptions.

To achieve the above-mentioned object, there are provided a method of providing whether a patient is accompanied by a caregiver and a device using the same according to an embodiment of the present disclosure. The method may include: receiving position data from devices of a patient and at least one caregiver; determining whether the patient is accompanied by the at least one caregiver on the basis of the position data of the patient and the at least one caregiver; and determining whether to generate a risk alarm to the patient on the basis of whether the patient is accompanied by the at least one caregiver that has been determined.

According to the present disclosure, the method may further include: setting a dangerous zone related to the patient before the receiving of the position data from the patient and the at least one caregiver.

According to the present disclosure, the dangerous zone may be at least one zone in which the probability of the occurrence of a fall accident of the patient is equal to or more than a first critical value.

According to the present disclosure, the method may further include: determining whether the patient is positioned in the dangerous zone on the basis of the position data of the patient before the determining of whether the patient is accompanied by the at least one caregiver.

According to the present disclosure, the method may further include: determining a dangerous time zone related to the patient before the receiving of the position data from the patient and the at least one caregiver.

According to the present disclosure, the method may further include: determining whether the patient is in the dangerous time zone on the basis of a current time when it is determined that the patient is positioned in the dangerous zone after the determining of whether the patient is positioned in the dangerous zone.

According to the present disclosure, in the determining of whether the patient is accompanied by the at least one caregiver, whether the patient is accompanied by the at least one caregiver may be determined by a proximity calculation method made with reference to a time difference between the position data of the patient and the at least one caregiver.

According to the present disclosure, the method may further include: mapping real-time position locating system (RTLS) data related to the patient and the at least one caregiver on the basis of an ASCII code before the determining of whether the patient is accompanied by the at least one caregiver.

According to the present disclosure, the mapping of the real-time position locating system (RTLS) data may further include removing the continuous ASCII code of the position data.

According to the present disclosure, the proximity calculation method may include: converting over time position routes of the patient and the at least one caregiver into character strings on the basis of a logical zone; and determining whether the patient is accompanied by the at least one caregiver on the basis of a length difference between character strings of the patient and the at least one caregiver.

To achieve the above-mentioned object, another embodiment of the present disclosure provides a device for providing whether a patient is accompanied by a caregiver. The device may include: a communication part; a storage part; and a processor operably connected to the communication part and the storage part, in which the processor is configured to receive position data from devices of a patient and at least one caregiver, determine whether the patient is accompanied by the at least one caregiver on the basis of the position data of the patient and the at least one caregiver, and determine whether to generate a risk alarm to the patient on the basis of whether the patient is accompanied by the at least one caregiver that has been determined.

According to the present disclosure, the processor may be further configured to set a dangerous zone related to the patient.

According to the present disclosure, the dangerous zone may be at least one zone in which the probability of the occurrence of a fall accident of the patient is equal to or more than a first critical value.

According to the present disclosure, the processor may be further configured to determine whether the patient is positioned in the dangerous zone on the basis of the position data of the patient.

According to the present disclosure, the processor may be further configured to set a dangerous time zone related to the patient.

According to the present disclosure, the processor may be further configured to determine whether the patient is in the dangerous time zone on the basis of a current time when it is determined that the patient is positioned in the dangerous zone.

According to the present disclosure, the processor may determine whether the patient is accompanied by the at least one caregiver by a proximity calculation method made with reference to a time difference between the position data of the patient and the at least one caregiver.

According to the present disclosure, the processor may be further configured to map real-time position locating system (RTLS) data related to the patient and the at least one caregiver on the basis of an ASCII code.

According to the present disclosure, the processor may be further configured to remove the continuous ASCII code of the position data.

According to the present disclosure, the proximity calculation method may be configured to convert over time position routes of the patient and the at least one caregiver into character strings on the basis of a logical zone and determine whether the patient is accompanied by the at least one caregiver on the basis of a length difference between character strings of the patient and the at least one caregiver.

Other detailed matters of the embodiment are included in the detailed description and the drawings.

The present disclosure may utilize the proximity calculation method performed in consideration of a time difference between position signals collected from the devices of the patient and the caregiver and prevent an error that occurs at the time of simply calculating a distance of the position data of the patient and the caregiver. Therefore, it is possible to improve the precision of the process of identifying whether the patient is accompanied by the caregiver.

In particular, the present disclosure may identify whether the patient is accompanied by the caregiver and generate an alarm to the caregiver in case that the patient wanders in the dangerous zone or wanders at the dangerous time when the patient is not accompanied by the caregiver. Therefore, it is possible to prevent a safety accident that may occur when the patient wanders alone.

The effects according to the present disclosure are not limited to the above-mentioned effects, and more various effects are included in the present disclosure.

BRIEF DESCRIPTION OF THE DRAWINGS

The above and other aspects, features and other advantages of the present disclosure will be more clearly understood from the following detailed description taken in conjunction with the accompanying drawings, in which:

FIGS. 6 to 11 are exemplified views of the method of providing whether the patient is accompanied by the caregiver according to the embodiment of the present disclosure.

DETAILED DESCRIPTION OF THE EMBODIMENT

Figure 1:
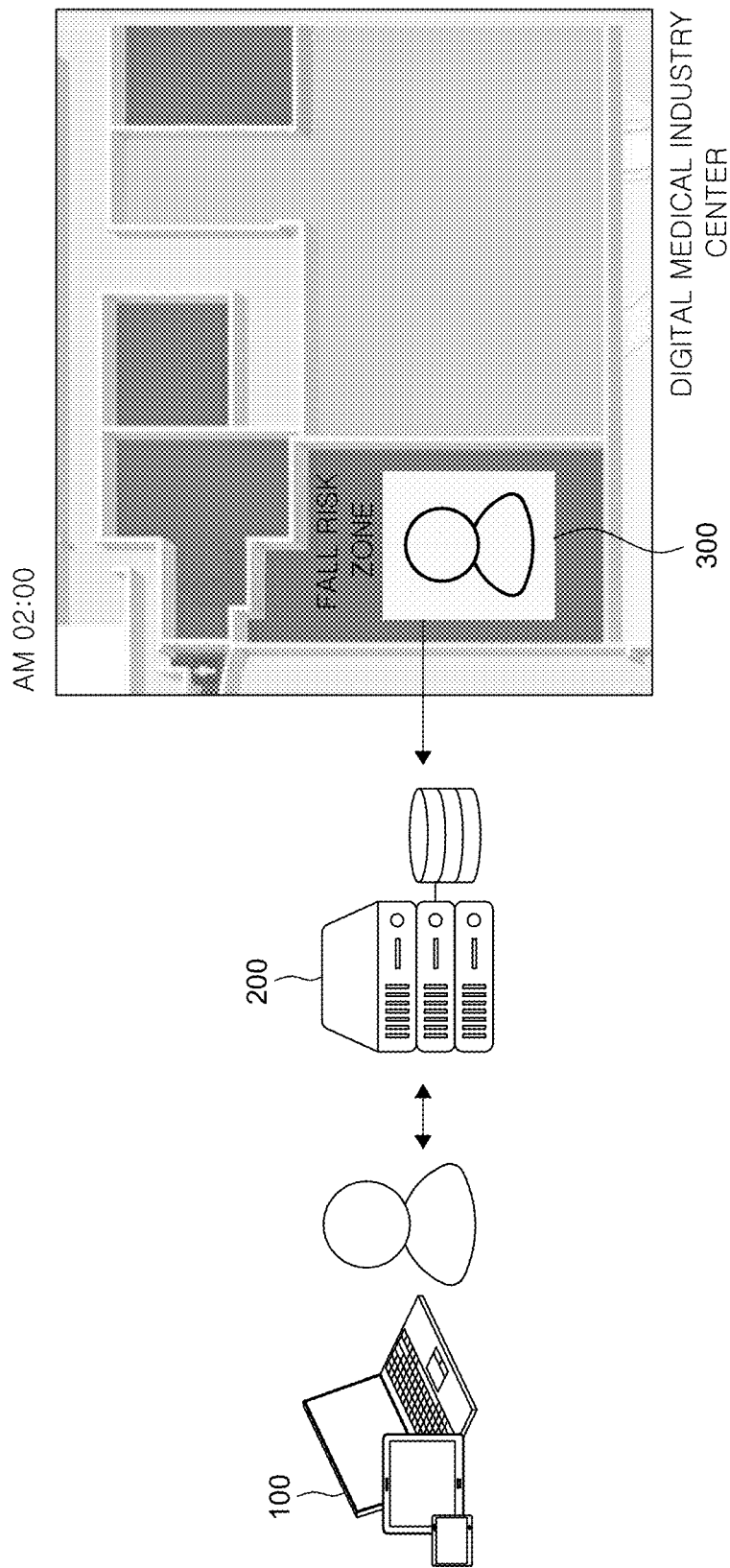
FIG. 1 is a schematic view of a system for providing whether a patient is accompanied by a caregiver, the system using a device for providing whether the patient is accompanied by the caregiver according to an embodiment of the present disclosure.

Advantages and features of the present disclosure and methods of achieving the advantages and features will be clear with reference to embodiments described in detail below together with the accompanying drawings. However, the present disclosure is not limited to the embodiments disclosed herein but will be implemented in various forms. The embodiments of the present disclosure are provided so that the present disclosure is completely disclosed, and a person with ordinary skill in the art to which the present disclosure pertains can fully understand the scope of the present disclosure. The present disclosure will be defined only by the scope of the appended claims. In connection with the description of the drawings, the similar reference numerals may be used for the similar components.

As used herein, the terms "have," "may have," "include," or "may include" indicate the existence of a feature (e.g., a number, function, operation, or a component such as a part) and do not exclude the existence of other features.

As used herein, the terms "A or B," "at least one of A and/or B," or "one or more of A and/or B" may include all possible combinations of A and B listed together. For example, "A or B," "at least one of A and B," "at least one of A or B" may indicate all of (1) including at least one A, (2) including at least one B, or (3) including at least one A and at least one B.

As used herein, the terms "first" and "second" may modify various components regardless of importance and do not limit the components. These terms are only used to distinguish one component from another. For example, a first user device and a second user device may indicate different user devices from each other regardless of the order or importance of the devices. For example, a first component may be named a second component, and similarly, the second component may also be named the first component, without departing from the scope disclosed in the present document.

It will be understood that when an element (e.g., a first element) is referred to as being (operatively or communicatively) "coupled with/to," or "connected with/to" another element (e.g., a second element), it can be coupled or connected with/to the other element directly or via a third element. In contrast, it will be understood that when an element (e.g., a first element) is referred to as being "directly coupled with/to" or "directly connected with/to" another element (e.g., a second element), no other element (e.g., a third element) intervenes between the element and the other element.

As used herein, the terms "configured (or set) to" may be interchangeably used with the terms "suitable for," "having the capacity to," "designed to," "adapted to," "made to," or "capable of" depending on circumstances. The term "configured (or set) to" does not essentially mean "specifically designed in hardware to." Rather, the term "configured to" may mean that a device can perform an operation together with another device or parts. For example, the term "processor configured (or set) to perform A, B, and C" may mean a generic-purpose processor (e.g., a central processing unit (CPU) or application processor) that may perform the operations by executing one or more software programs stored in a memory device or a dedicated processor (e.g., an embedded processor) for performing the operations.

The terms used in the present document are used to just describe a specific embodiment and do not intend to limit the scope of another embodiment. Singular expressions may include plural expressions unless clearly described as different meanings in the context. The terms used herein, including technical or scientific terms, may have the same meaning as commonly understood by those skilled in the art disclosed in the present document. The terms such as those defined in commonly used dictionaries may be interpreted as having meanings identical or similar to meanings in the context of related technologies and should not be interpreted as ideal or excessively formal meanings unless explicitly defined in the present document. In some instances, the terms defined in the present document should not be interpreted to exclude the embodiments disclosed in the present document.

Respective features of several embodiments of the present disclosure may be partially or entirely coupled to or combined with each other, and as sufficiently appreciated by those skilled in the art, various technical cooperation and operations may be made, and the respective embodiments may be carried out independently of each other or carried out together correlatively.

The terms used in the present specification are defined as follows to clearly describe the present specification.

FIG. 1 is a schematic view of a system for providing whether a patient is accompanied by a caregiver, the system using a device for providing whether the patient is accompanied by the caregiver according to an embodiment of the present disclosure.

With reference to FIG. 1, a system 1000 for providing whether a patient is accompanied by a caregiver includes a user device 100, a user interface providing server 200 (hereinafter, referred to as a server 200 for providing whether the patient is accompanied by the caregiver), and a position transmitter 300.

The system 1000 for providing whether the patient is accompanied by the caregiver may receive position information from a device of the patient and a device of the caregiver and identify whether the patient is positioned in a dangerous zone in a dangerous time zone on the basis of the position information. In case that the patient is positioned in the dangerous zone in the dangerous time zone, the system 1000 may provide whether the patient is accompanied by the caregiver. In this case, in case that the patient is positioned in the dangerous zone in the dangerous time zone without being accompanied by the caregiver, the system 1000 for providing whether the patient is accompanied by the caregiver may transmit an alarm to the user device 100. In this case, the system 1000 for providing whether the patient is accompanied by the caregiver may include the user device 100 configured to receive information on the positions of the patient and the caregiver and receive an alarm when the patient wanders in the dangerous zone in the dangerous time zone without being accompanied by the caregiver, the server 200 for providing whether the patient is accompanied by the caregiver, the server 200 being configured to determine whether the patient is accompanied by the caregiver on the basis of the received position information, and the position transmitter 300 configured to transfer information on the positions of the patient and the caregiver.

Specifically, the user device 100 may be a device configured to provide a user interface for providing a result of determining whether the patient is accompanied by the caregiver. In this case, the user device 100 may receive a result of determining whether the patient is accompanied by the caregiver from the server 200 for providing whether the patient is accompanied by the caregiver, and the user device 100 may display the received result. In this case, the user device 100 may be an electronic device capable of capturing an image and outputting the image and include a smartphone, a tablet PC, a PC, a laptop computer, or the like.

The server 200 for providing whether the patient is accompanied by the caregiver may receive the information on the positions of the patient and the caregiver from the position transmitter 300. In this case, the server 200 for providing whether the patient is accompanied by the caregiver may determine whether the patient is accompanied by the caregiver when the position information indicates that the patient is positioned in the dangerous zone in the dangerous time zone. In this case, the server 200 for providing whether the patient is accompanied by the caregiver may generate a notification related to the patient to the user device 100 when the server 200 determines that the patient is not accompanied by the caregiver. The position transmitter 300 may be a device for providing information on the positions of the patient and the caregiver. In this case, the position transmitter 300 may be an electronic device capable of transmitting the position and include a smartphone, a Bluetooth transmitter, a Bluetooth low-energy protocol, or the like.

Figure 2:
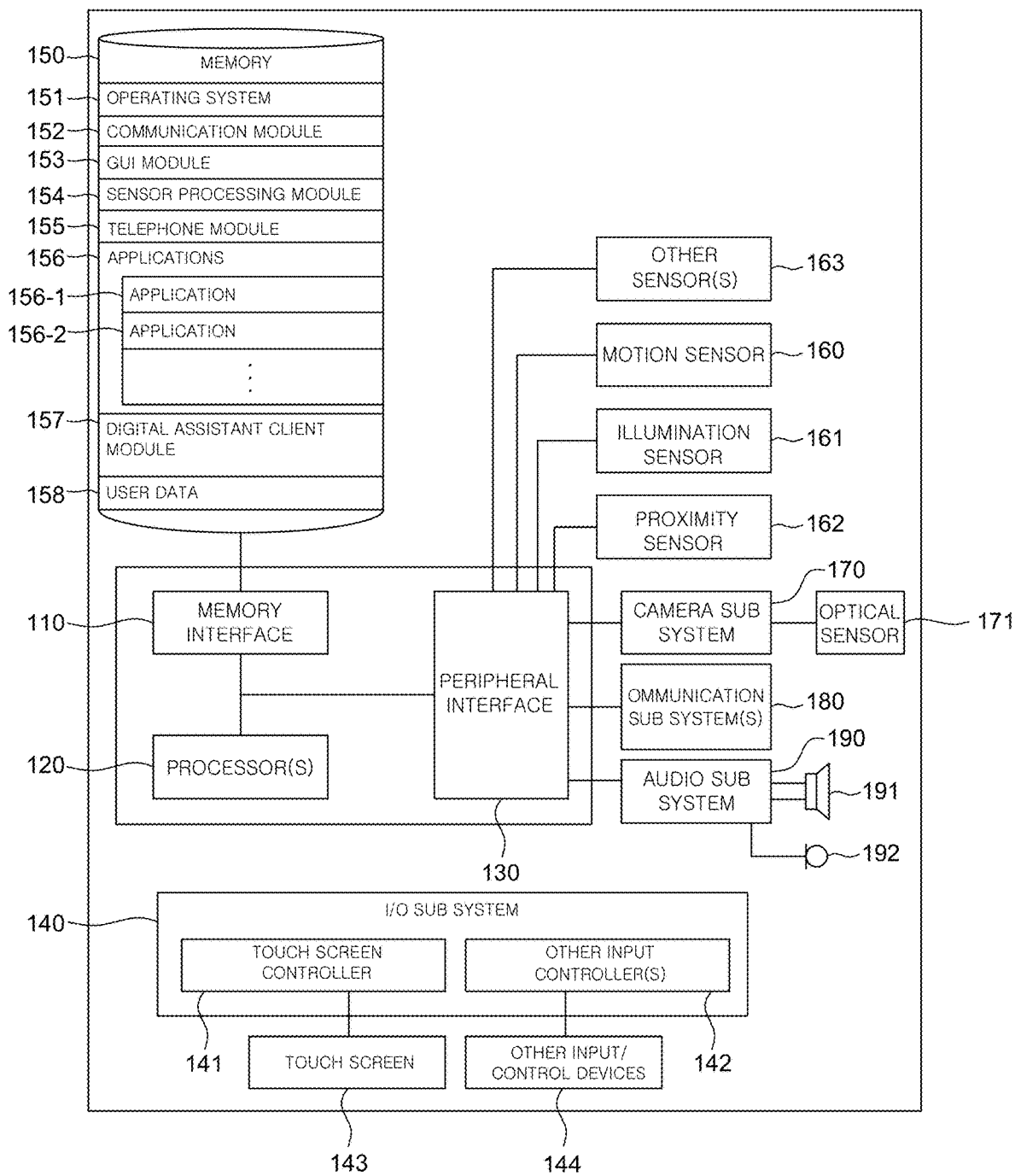
FIG. 2 is a block diagram illustrating a configuration of a user device according to the embodiment of the present disclosure.

FIG. 2 is a block diagram illustrating a configuration of the user device according to the embodiment of the present disclosure.

With reference to FIG. 2, the user device 100 may include a memory interface 110, one or more processors 120, and a peripheral interface 130. Various components in the user device 100 may be connected by one or more communication buses or signal lines.

The memory interface 110 may be connected to a memory 150 and transmit various data to the processor 120. In this case, the memory 150 may include at least one type of storage medium among a flash memory, a hard disc, a multimedia card micro-memory, a card type memory (e.g., an SD or XD memory, or the like), a RAM, an SRAM, a ROM, an EEPROM, a PROM, a network storage, cloud, and a block-chain database.

In various embodiments, the memory 150 may store at least one of an operating system 151, a communication module 152, a graphic user interface module (GUI) 153, a sensor processing module 154, a telephone module 155, and an application module 156. Specifically, the operating system 151 may include a command for processing a basic system service and a command for performing hardware tasks. The communication module 152 may communicate with at least one of one or more other devices, computers, and servers. The graphic user interface module (GUI) 153 may process a graphic user interface. The sensor processing module 154 may process a sensor-related function (e.g., process a voice input received by using one or more microphones 192). The telephone module 155 may process a telephone-related function. The application module 156 may perform various functions of the user application, such as electronic messaging, web browsing, media processing, searching, imaging, or other process functions. Further, the user device 100 may store one or more software applications 156-1 and 156-2 related to any one type of service in the memory 150. In this case, the application 156-1 may provide the user device 100 with the information on the system for providing whether the patient is accompanied by the caregiver.

In various embodiments, the memory 150 may store a digital assistant client module 157 (hereinafter, referred to as a DA client module) and thus store commands for performing a function of the client of the digital assistant and various user data 158 (e.g., other data such as user-customized vocabulary data, preference data, a user electronic address book, a to-do list, or a shopping list).

Meanwhile, the DA client module 157 may acquire voice input, text input, touch input and/or gesture input of the user by means of various user interfaces (e.g., a I/O sub-system 140) equipped in the user device 100.

In addition, the DA client module 157 may output audio-visual or tactile data. For example, the DA client module 157 may output data formed of a combination of at least two or more of voice, sound, a notice, a text message, a menu, a graphic, a video, an animation, and a vibration. Further, the DA client module 157 may communicate with a digital assistant server (not illustrated) using a communication sub-system 180.

In various embodiments, the DA client module 157 may collect additional information on the surrounding environment of the user device 100 from various sensors, sub-systems, and peripheral devices to configure a context associated with the user input. For example, the DA client module 157 may infer the intention of the user by providing context information to the digital assistant server together with the user input. In this case, the context information may be accompanied by the user input may include sensor information, such as light, ambient noises, ambient temperature, an image of the surrounding environment, and a video. As another example, the context information may include a physical state (e.g., a device orientation, a device position, a device temperature, a power level, a speed, an acceleration, a motion pattern, or a cellular signal intensity) of the user device 100. As another example, the context information may include information related to a software state of the user device 100 (e.g., a process that is being executed, installed program, past and present network activities, a background service, an error log, or resource usage in the user device 100).

In various embodiments, the memory 150 may include added or deleted commands. Further, the user device 100 may also include additional configurations other than the configurations illustrated in FIG. 2 or exclude some configurations.

The processor 120 may control an overall operation of the user device 100 and execute an application or a program stored in the memory 150 to perform various commands.

The processor 120 may correspond to an arithmetic device such as a central processing unit (CPU) or an application processor (AP). In addition, the processor 120 may be implemented as an integrated chip (IC) such as a system on chip (SoC) with which various arithmetic devices, such as a neural processing unit (NPU), are integrated.

The peripheral interface 130 is connected to various sensors, sub-systems, and peripheral devices to provide data to allow the user device 100 to perform various functions. In this case, the configuration in which the user device 100 performs any function may be understood as a configuration in which the function is performed by a processor 120.

The peripheral interface 130 may receive data from a motion sensor 160, an illumination sensor (an optical sensor) 161, and a proximity sensor 162. Therefore, the user device 100 may perform orientation, lighting, and proximity sensing functions. As another example, the peripheral interface 130 may be provided with data from other sensors 163 (a positioning system-GPS receiver, a temperature sensor, or a biometric sensor), and thus the user device 100 may perform functions related to the other sensors 163.

In various embodiments, the user device 100 may include a camera sub-system 170 connected to the peripheral interface 130 and an optical sensor 171 connected thereto, and thus the user device 100 may perform various photographing functions such as taking a picture or recording a video clip.

In various embodiments, the user device 100 may include the communication sub-system 180 connected to the peripheral interface 130. The communication sub-system 180 may be configured by one or more wired/wireless networks and may include various communication ports, a wireless frequency transceiver, and an optical transceiver.

In various embodiments, the user device 100 includes an audio sub-system 190 connected to the peripheral interface 130, and the audio sub-system 190 includes one or more speakers 191 and one or more microphones 192 so that the user device 100 may perform voice-operated functions, such as voice recognition, voice duplication, digital recording, and telephone functions.

In various embodiments, the user device 100 may include an I/O sub-system 140 connected to the peripheral interface 130. For example, the I/O sub-system 140 may control the touch screen 143 included in the user device 100 by means of a touch screen controller 141. For example, the touch screen controller 141 may use any one of a plurality of touch sensing techniques such as a capacitive type, a resistive type, an infrared type, a surface acoustic wave technology, or a proximity sensor array to detect contact and movement of the user or stopping of contact and movement. As another example, the I/O sub-system 140 may control the other input/control device 144 included in the user device 100 by means of other input controller(s) 142. For example, the other input controller(s) 142 may control one or more buttons, rocker switches, thumb-wheels, infrared ports, USB ports, and pointer devices such as a stylus.

Figure 3:
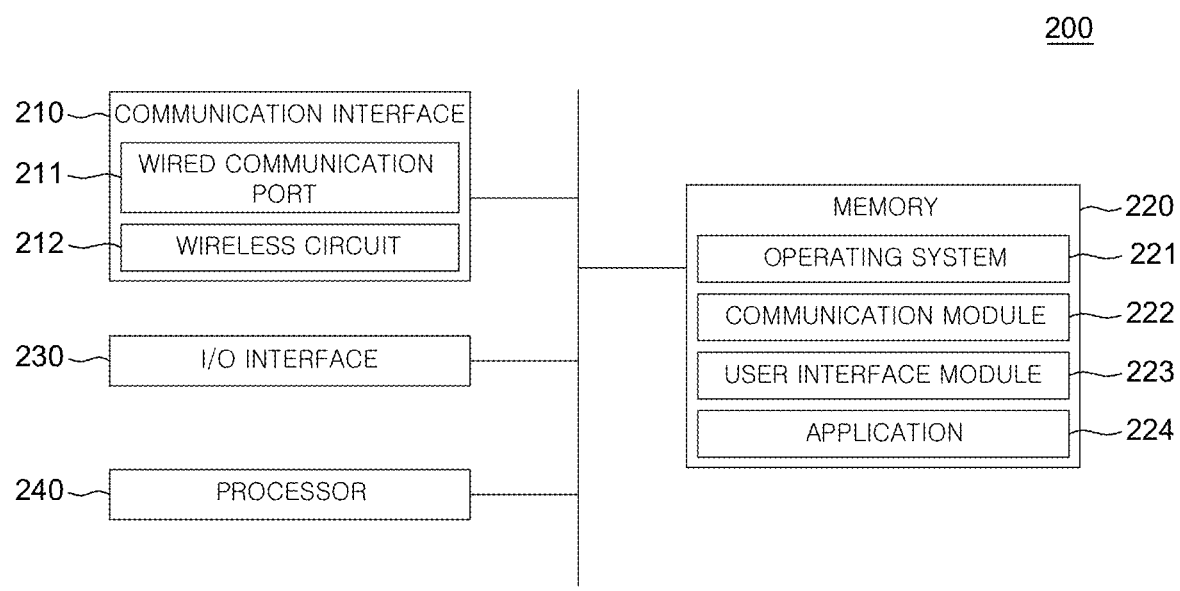
FIG. 3 is a block diagram illustrating a configuration of a server for providing whether the patient is accompanied by the caregiver according to the embodiment of the present disclosure.

FIG. 3 is a block diagram illustrating a configuration of the server for providing whether the patient is accompanied by the caregiver according to the embodiment of the present disclosure.

With reference to FIG. 3, the server 200 for providing whether the patient is accompanied by the caregiver may include a communication interface 210, a memory 220, a I/O interface 230, and a processor 240. The respective components may communicate with one another via one or more communication buses or signal lines.

The communication interface 210 may be connected to the user devices 100 via a wired/wireless communication network to exchange data. For example, the communication interface 210 may receive human data of the patient and the caregiver from the user device 100. In this case, the human data of the patient and the caregiver may be information on a name of the patient, a name of the caregiver, an inherent identification, a risk level, an inherent position device key, and the like. In addition, the communication interface 210 may receive position data of the patient and the caregiver from the position transmitter 300. In this case, the inherent position device key may be respective identification values related to the position transmitter 300. Meanwhile, the communication interface 210 may transmit an alarm to the user device 100 when the patient is positioned in the dangerous zone in the dangerous time zone without being accompanied by the caregiver.

Meanwhile, the communication interface 210, which enables the transmission/reception of the data, includes a wired communication port 211 and a wireless circuit 212. In this case, the wired communication port 211 may include one or more wired interfaces, for example, Ethernet, universal serial bus (USB), FireWire, and the like. In addition, the wireless circuit 212 may transmit and receive data with external devices by an RF signal or an optical signal. In addition, the wireless communication may use at least one of a plurality of communication standards, protocols, and technologies, for example, GSM, EDGE, CDMA, TDMA, Bluetooth, Wi-Fi, VoIP, Wi-Max, or other arbitrary appropriate communication protocols.

The memory 220 may store various data used for the server 200 for providing whether the patient is accompanied by the caregiver. For example, the memory 220 may store dangerous zone setting data, dangerous time setting data, fall probability for each zone, user data, and the like.

In various embodiments, the memory 220 may include a volatile or non-volatile recording medium capable of storing various types of data, commands, and information. For example, the memory 220 may include at least one type of storage medium among a flash memory, a hard disc, a multimedia card micro-memory, a card type memory (e.g., an SD or XD memory, or the like), a RAM, an SRAM, a ROM, an EEPROM, a PROM, a network storage, cloud, and a block-chain database.

In various embodiments, the memory 220 may store a configuration of at least one of an operating system 221, a communication module 222, a user interface module 223, and one or more applications 224.

The operating system 221 (e.g., an embedded operating system, such as LINUX, UNIX, MAC OS, WINDOWS, VxWorks) may include various software components and drivers that control and manage a general system task (e.g., memory management, storage device control, or power management) and support communication between various hardware, firmware, and software components.

The communication module 223 may support communication with another device through the communication interface 210. The communication module 220 may include various software components for processing data received by a wired communication port 211 or a wireless circuit 212 of the communication interface 210.

The user interface module 223 may receive a request or an input of the user from a keyboard, a touch screen, or a microphone via the I/O interface 230 and provide the user interface on the display.

The application 224 may include a program or a module configured to be executed by one or more processors 230. In this case, an application for providing a result of determining whether the patient is accompanied by the caregiver may be implemented on a server farm.

The I/O interface 230 may connect at least one of input/output devices (not illustrated) of the server 200 for providing whether the patient is accompanied by the caregiver, e.g., a display, a keyboard, a touch screen, and a microphone, to the user interface module 223. The I/O interface 230 receives the user input (e.g., voice input, keyboard input, or touch input) together with the user interface module 223 and processes a command in accordance with the received input.

The processor 240 may be connected to the communication interface 210, the memory 220, and the I/O interface 230 to control the overall operation of the server 200 for providing whether the patient is accompanied by the caregiver. Further, the processor 240 may perform various commands for the result of providing whether the patient is accompanied by the caregiver by means of the application or program stored in the memory 220.

The processor 240 may correspond to an arithmetic device such as a central processing unit (CPU) or an application processor (AP). Further, the processor 240 may be implemented as an integrated chip (IC) such as a system on chip (SoC) with which various arithmetic devices are integrated. Alternatively, the processor 240 may include a module for calculating an artificial neural network model like a neural processing unit (NPU).

In various embodiments, the processor 240 may receive position data from the position transmitter that transmits the positions of the patient and the caregiver. In this case, the processor 240 may set in advance a dangerous zone related to the patient. In this case, the processor 240 may set a zone, in which the probability of the occurrence of the safety accident of the patient in the zone in the hospital is equal to or more than a first critical value, to the dangerous zone. For example, the first critical value may be 50%. In this case, the first critical value may be set to vary depending on the user's determination. Meanwhile, the processor 240 may set in advance a dangerous time related to the patient. In this case, the dangerous time may be set to 22 to 06. In this case, the dangerous time may be set to vary depending on the user's determination.

The processor 240 may determine whether the patient is accompanied by the caregiver on the basis of the position data of the patient and the caregiver. In this case, when the patient is positioned in the dangerous zone at the dangerous time, the processor 240 may determine whether the patient is accompanied by the caregiver. In this case, the processor 240 may determine whether the patient is accompanied by the caregiver by a proximity calculation method made with reference to the time difference between the position data of the patient and the caregiver. In this case, the proximity calculation method may convert position routes of the patient and the caregiver over time into character strings on the basis of a logical zone and determine whether the patient is accompanied by the caregiver on the basis of a length difference between the character strings of the patient and the caregiver.

The processor 240 may determine whether to generate an alarm to the patient on the basis of whether the patient is accompanied by the caregiver that has been determined. In this case, in case that the processor 240 determines that the patient is accompanied by the caregiver, the processor 240 may not generate an alarm. In this case, the processor 240 may generate an alarm when the patient is positioned in the dangerous zone at the dangerous time without being accompanied by the caregiver. In addition, the processor 240 may provide the generated alarm to the user device 100.

Figure 4:
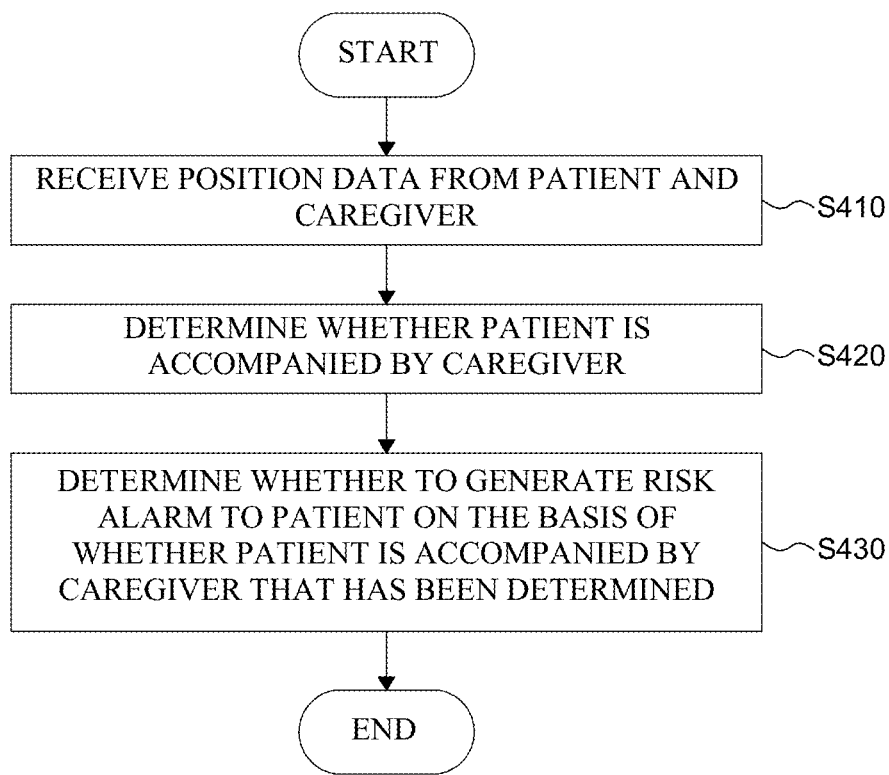
FIGS. 4 and 5 is a flowchart of a method of providing whether a patient is accompanied by a caregiver according to the embodiment of the present disclosure.
Figure 5:
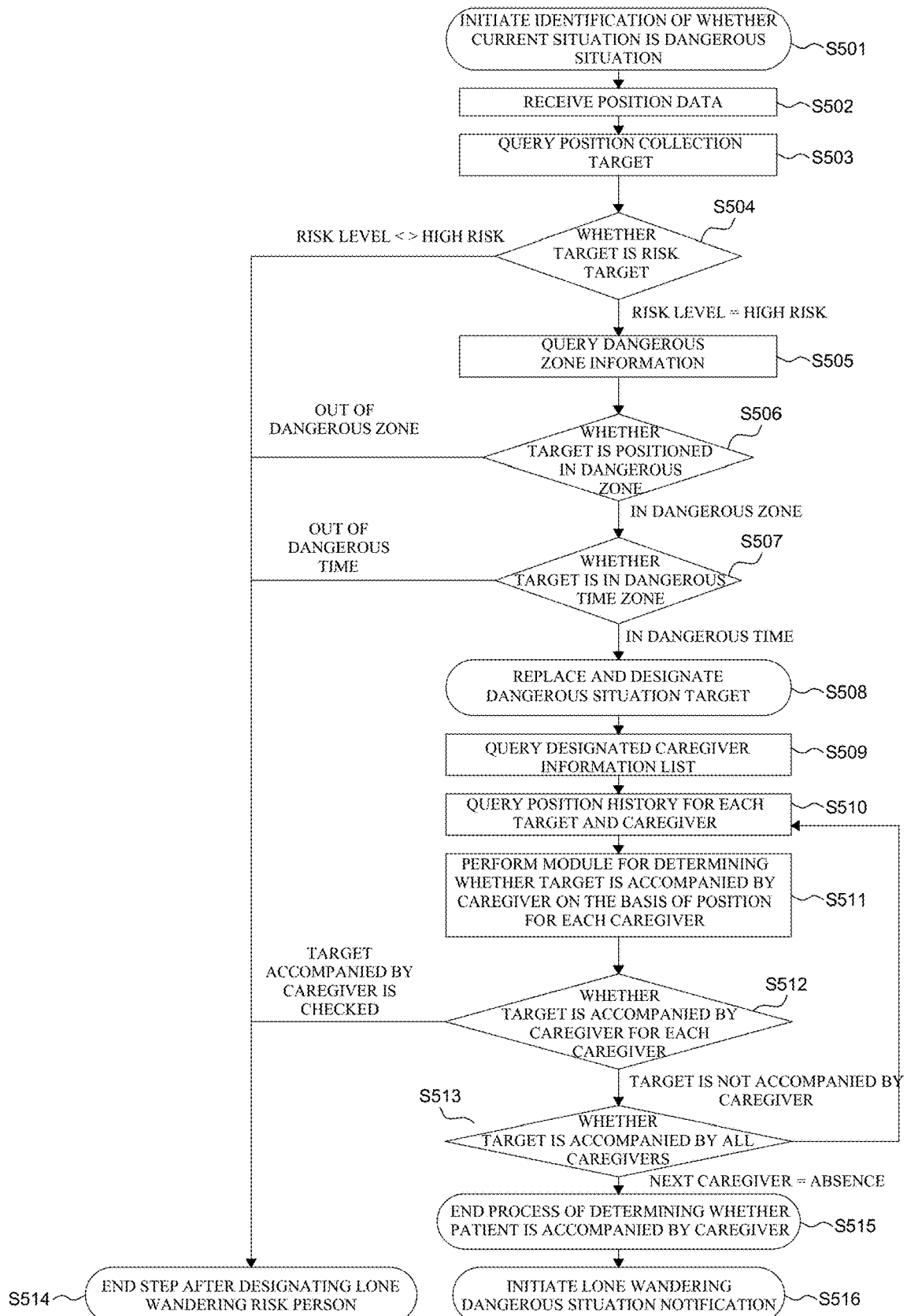

FIGS. 4 and 5 is a flowchart of a method of providing whether a patient is accompanied by a caregiver according to the embodiment of the present disclosure, and FIGS. 6 to 11 are exemplified views of the method of providing whether the patient is accompanied by the caregiver according to the embodiment of the present disclosure.

First, with reference to FIG. 4, the server 200 for providing whether the patient is accompanied by the caregiver receives the position data from the patient and the caregiver (S410). In this case, the position data of the patient and the caregiver may be received from the devices owned by the patient and the caregiver. In another embodiment, the position data of the patient and the caregiver may be received from position collection devices corresponding to the patient and the caregiver. Meanwhile, the server 200 for providing whether the patient is accompanied by the caregiver may set in advance the dangerous zone related to the patient. In this case, the server 200 for providing whether the patient is accompanied by the caregiver may set a zone, in which the probability of the occurrence of the safety accident of the patient in the zone in the hospital is equal to or more than the first critical value, to the dangerous zone. For example, the first critical value may be 50%. In this case, the first critical value may be set to vary depending on the user's determination. Meanwhile, the server 200 for providing whether the patient is accompanied by the caregiver may set in advance the dangerous time related to the patient. In this case, the dangerous time may be set to 22 to 06. In this case, the dangerous time may be set to vary depending on the user's determination.

Next, the server 200 for providing whether the patient is accompanied by the caregiver may determine whether the patient is accompanied by the caregiver (S420). In this case, when the patient is positioned in the dangerous zone at the dangerous time, the server 200 for providing whether the patient is accompanied by the caregiver may determine whether the patient is accompanied by the caregiver. In this case, the server 200 for providing whether the patient is accompanied by the caregiver may determine whether the patient is accompanied by the caregiver by the proximity calculation method made with reference to the time difference between the position data of the patient and the caregiver. In this case, the proximity calculation method may convert position routes of the patient and the caregiver over time into the character strings on the basis of the logical zone and determine whether the patient is accompanied by the caregiver on the basis of the length difference between the character strings of the patient and the caregiver.

Next, the server 200 for providing whether the patient is accompanied by the caregiver determines whether to generate an alarm to the patient on the basis of whether the patient is accompanied by the caregiver that has been determined (S430). In this case, in case that the server 200 determines that the patient is accompanied by the caregiver, the server 200 for providing whether the patient is accompanied by the caregiver may not generate an alarm. In this case, when the patient is positioned in the dangerous zone at the dangerous time without being accompanied by the caregiver, the server 200 for providing whether the patient is accompanied by the caregiver may generate an alarm.

The flowchart of the method of providing whether the patient is accompanied by the caregiver according to the embodiment of the present disclosure has been described above. Hereinafter, the method of providing whether the patient is accompanied by the caregiver will be described in more detail with reference to the exemplified views.

With reference to FIG. 5, the server 200 for providing whether the patient is accompanied by the caregiver initiates a process of identifying whether the current situation is a dangerous situation (S501). In this case, the server 200 for providing whether the patient is accompanied by the caregiver may set a risk target and a caregiver on which the determination of whether the patient is accompanied by the caregiver is performed. In this case, a risk target may be a patient.

For example, the server 200 for providing whether the patient is accompanied by the caregiver may set data related to the risk target. In this case, the data related to the risk target may include a target name, a target ID, an inherent position device key, a risk level, and the like. In this case, the target name may be a name of the risk target, the target ID may be an inherent identification of the risk target, the inherent position device key may be an inherent key value of the position transmitter carried by the risk target, and the risk level may be a degree of danger when the corresponding target is positioned alone. For example, the target name may be set to Gil-dong Hong, the target ID may be set to H1, the inherent position device key may be set to DEV000001, and the risk level may be set to a high risk.

Meanwhile, the server 200 for providing whether the patient is accompanied by the caregiver may set the data related to the caregiver. In this case, the data related to the caregiver may include a caregiver name, a caregiver ID, an inherent position device key, a protection target ID, and the like. In this case, the caregiver name may be a name of the caregiver, the caregiver ID is an inherent identification of the caregiver, the inherent position device key may be an inherent key value of the position transmitter carried by the caregiver, and the protection target ID may be an inherent number of the risk target matched with the caregiver target. For example, the caregiver name may be set to Gan-byeong Kim, the caregiver ID may be set to C1, the inherent position device key may be set to DEV000002, and the protection target ID may be set to H1. In this case, the server 200 for providing whether the patient is accompanied by the caregiver may designate a plurality of caregivers to a single risk target.

In this case, the server 200 for providing whether the patient is accompanied by the caregiver may set matching data of the risk target and the caregiver. In this case, the matching data of the risk target and the caregiver may include names, IDs, user divisions, risk levels, protection target IDs, inherent position device keys, and the like. For example, the names may be set to Gil-dong Hong and Gan-byeong Kim, the IDs may be set to H1 and C1, the user divisions may be set to the target and the caregiver, the risk levels may be set to the high risk and—, the protection target IDs may be set to—and H1, and the inherent position device keys may be set to DEV000001 and DEV000002.

Meanwhile, the server 200 for providing whether the patient is accompanied by the caregiver may set in advance the dangerous zone and the dangerous time of the patient.

Figure 6:
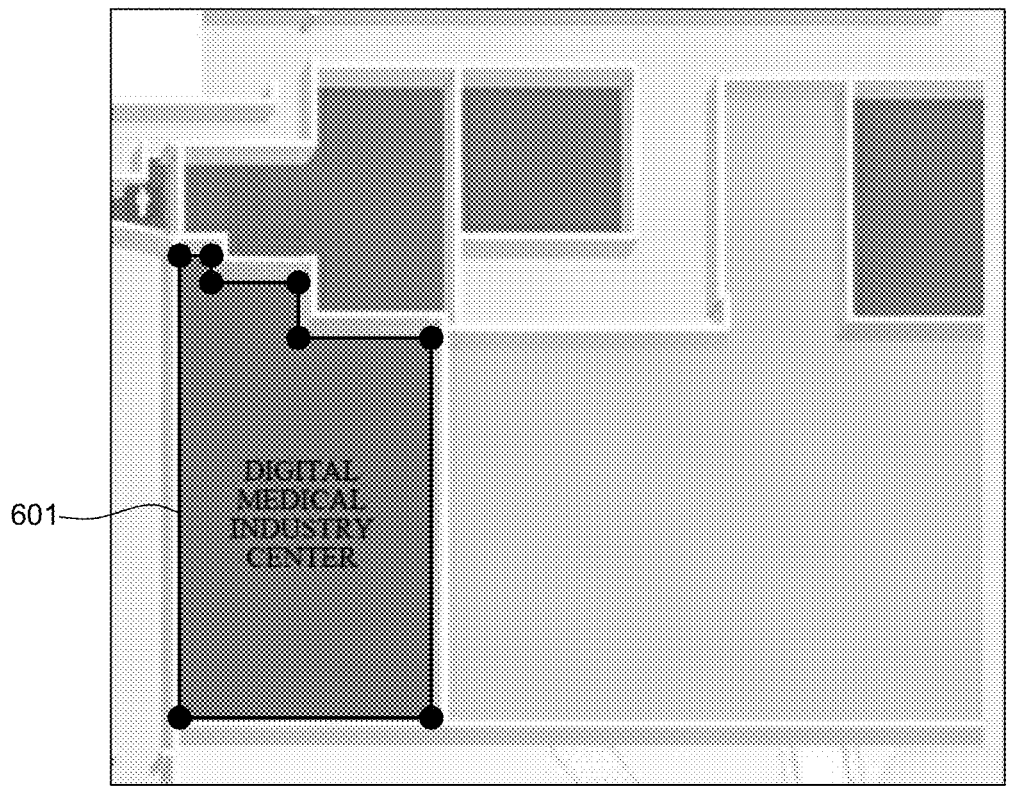
Figure 8:
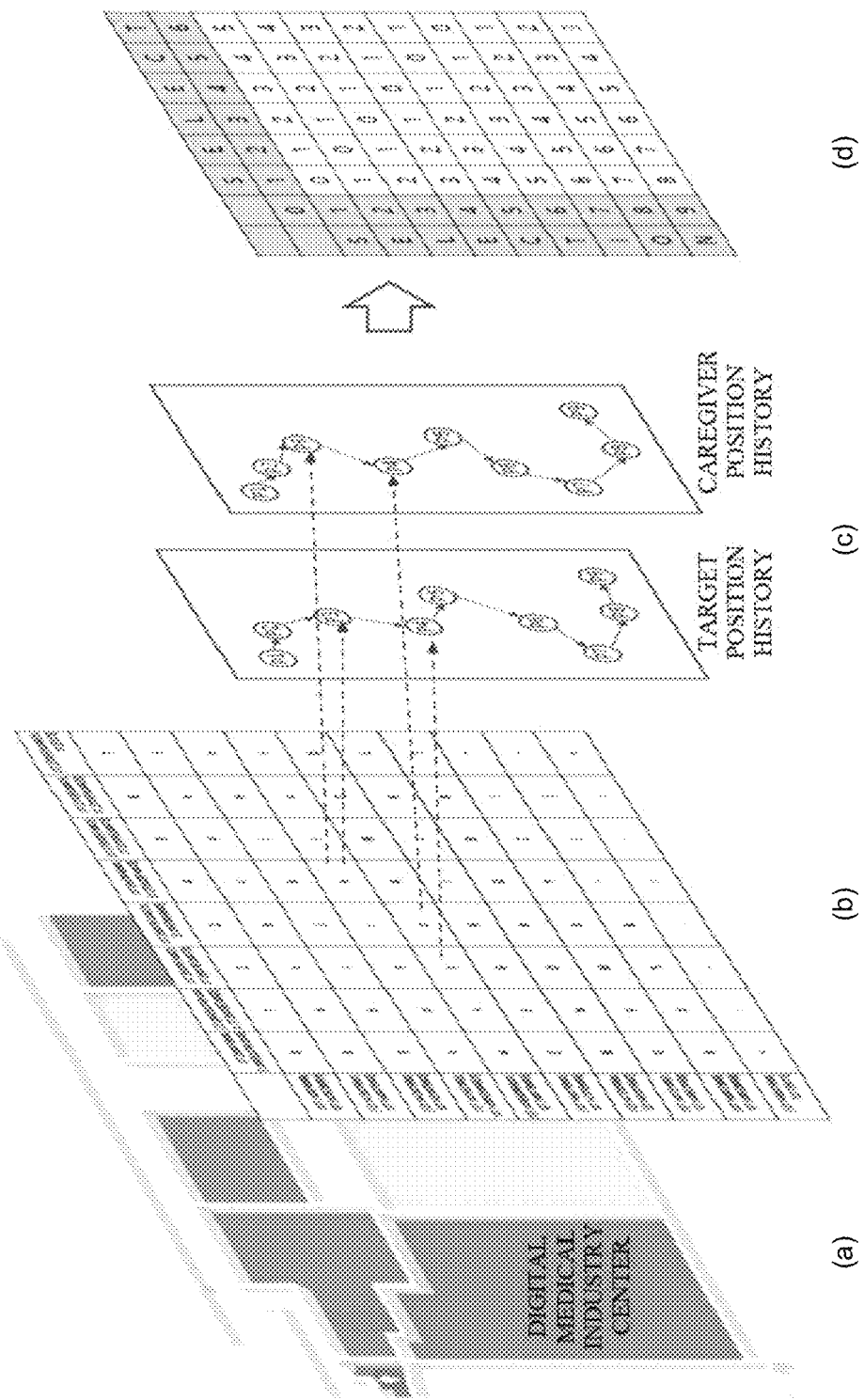

More specifically, with reference to FIG. 6, the server 200 for providing whether the patient is accompanied by the caregiver may set zones in the hospital on the basis of drawings of the interior of the hospital. In this case, the server 200 for providing whether the patient is accompanied by the caregiver may set a zone 1601 in a polygonal shape. In this case, the server 200 for providing whether the patient is accompanied by the caregiver may set a zone name, a zone ID, and a zone configuration coordinate of the zone 1601, set whether the zone is the dangerous zone, and set the dangerous time. In this case, the zone name may be a name of the zone. In this case, the zone ID may be an inherent value for identifying a preset zone. In addition, the zone configuration coordinate may be an assembly and sequence of coordinates for identifying a range of a preset zone. In this case, whether the zone is the dangerous zone may be a value made by setting the preset zone is the dangerous zone. In this case, the dangerous time may be a dangerous time zone when the patient is positioned alone in the preset zone.

For example, the zone name of the zone 1601 may be set to fall risk zone 1, the zone ID may be set to A1, the zone configuration coordinate may be set to P1 (X1, Y1), P2 (X2, Y2), and PN (XN, YN), whether the zone is the dangerous zone may be set to Y, and the dangerous time may be set to a whole day.

With reference back to FIG. 5, the server 200 for providing whether the patient is accompanied by the caregiver receives the position data (S502). In this case, the server 200 for providing whether the patient is accompanied by the caregiver may receive the position data of the patient and the caregiver. In this case, the server 200 for providing whether the patient is accompanied by the caregiver may receive information on inherent device numbers, position coordinates, collection time, and the like. For example, the inherent device number may be received as DEV000001, the position coordinate may be received as CP (CX1, CY1), and the collection time may be received as eleven thirteen minutes and twelve seconds.

Next, the server 200 for providing whether the patient is accompanied by the caregiver queries a position collection target (S503). In this case, the server 200 for providing whether the patient is accompanied by the caregiver may receive information on the target to which the device is assigned on the basis of the inherent device number of the risk target.

For example, with reference to FIG. 7A, the information on the position collection target may include Gil-dong Hong, H1, the target, the high risk, DEV000001, and the like.

With reference back to FIG. 5, the server 200 for providing whether the patient is accompanied by the caregiver determines whether the position collection target is the risk target (S504). In this case, the server 200 for providing whether the patient is accompanied by the caregiver may determine whether the position collection target is the risk target on the basis of the information on the position collection target. In this case, in case that the server 200 determines that the risk level of the position collection target is the risk target, the server 200 for providing whether the patient is accompanied by the caregiver queries the information on the dangerous zone (S505).

For example, with reference to FIG. 7B, the information on the dangerous zone may be received as fall risk zone 1, the zone ID may be received as A1, the zone configuration coordinate may be received as P1 (X1, Y1), P2 (X2, Y2), and PN (XN, YN), whether the zone is the dangerous zone may be received as Y, and the dangerous time may be received as a whole day.

With reference back to FIG. 5, in case that the server 200 does not determine that the risk level of the position collection target is the risk target, the server 200 for providing whether the patient is accompanied by the caregiver ends the process of determining whether the patient is accompanied by the caregiver (S514).

Next, the server 200 for providing whether the patient is accompanied by the caregiver determines whether the position collection target is positioned in the dangerous zone (S506). In this case, in case that the server 200 determines that the position collection target is positioned in the dangerous zone, the server 200 for providing whether the patient is accompanied by the caregiver determines whether the position collection target is positioned in the dangerous time zone (S507). Meanwhile, in case that the server 200 determines that the position collection target is positioned outside the dangerous zone, the server 200 for providing whether the patient is accompanied by the caregiver ends the process of determining whether the patient is accompanied by the caregiver (S514).

Next, the server 200 for providing whether the patient is accompanied by the caregiver determines whether the position collection target is in the dangerous time zone (S507). In this case, the server 200 for providing whether the patient is accompanied by the caregiver may determine whether the position collection target is in the dangerous time zone on the basis of the information received in the position data receiving step S502. In this case, in case that the server 200 determines that the position collection target is in the dangerous time, the server 200 for providing whether the patient is accompanied by the caregiver designates a dangerous situation target (S508). In this case, the server 200 for providing whether the patient is accompanied by the caregiver may designate the position collection target to the dangerous situation target.

For example, with reference to FIG. 7C, the data for designating the position collection target to the dangerous situation target may be received as Gil-dong Hong, H1, fall risk zone 1, A1, and dangerous situation=Y.

With reference back to FIG. 5, in case that the server 200 determines that the position collection target is out of the dangerous time, the server 200 for providing whether the patient is accompanied by the caregiver ends the process of determining whether the patient is accompanied by the caregiver (S514).

Next, the server 200 for providing whether the patient is accompanied by the caregiver queries a designated caregiver information list (S509). In this case, the server 200 for providing whether the patient is accompanied by the caregiver may receive data related to the caregiver matched with the dangerous situation target.

For example, with reference to FIG. 7D, the data related to the caregiver matched with the dangerous situation target may be received as Gan-byeong Kim, C1, the caregiver, H1, and EV000002.

With reference back to FIG. 5, the server 200 for providing whether the patient is accompanied by the caregiver queries position history for each dangerous situation target and each caregiver (S510). In this case, the server 200 for providing whether the patient is accompanied by the caregiver may query the position history for each dangerous situation target and each caregiver by means of a logical zone on the drawing and the map.

More specifically, with reference to FIG. 8A, the server 200 for providing whether the patient is accompanied by the caregiver may set the zone with reference to an actual drawing of the hospital. In this case, with reference to FIG. 8B, the server 200 for providing whether the patient is accompanied by the caregiver may divide the zone on the basis of the maximum/minimum latitude and longitude of the hospital that may be measured by a real-time locating system (RTLS). For example, the zone may be divided into 80 zones. In this case, the server 200 for providing whether the patient is accompanied by the caregiver may provide a single ASCII code to each of the zones.

Figure 9:
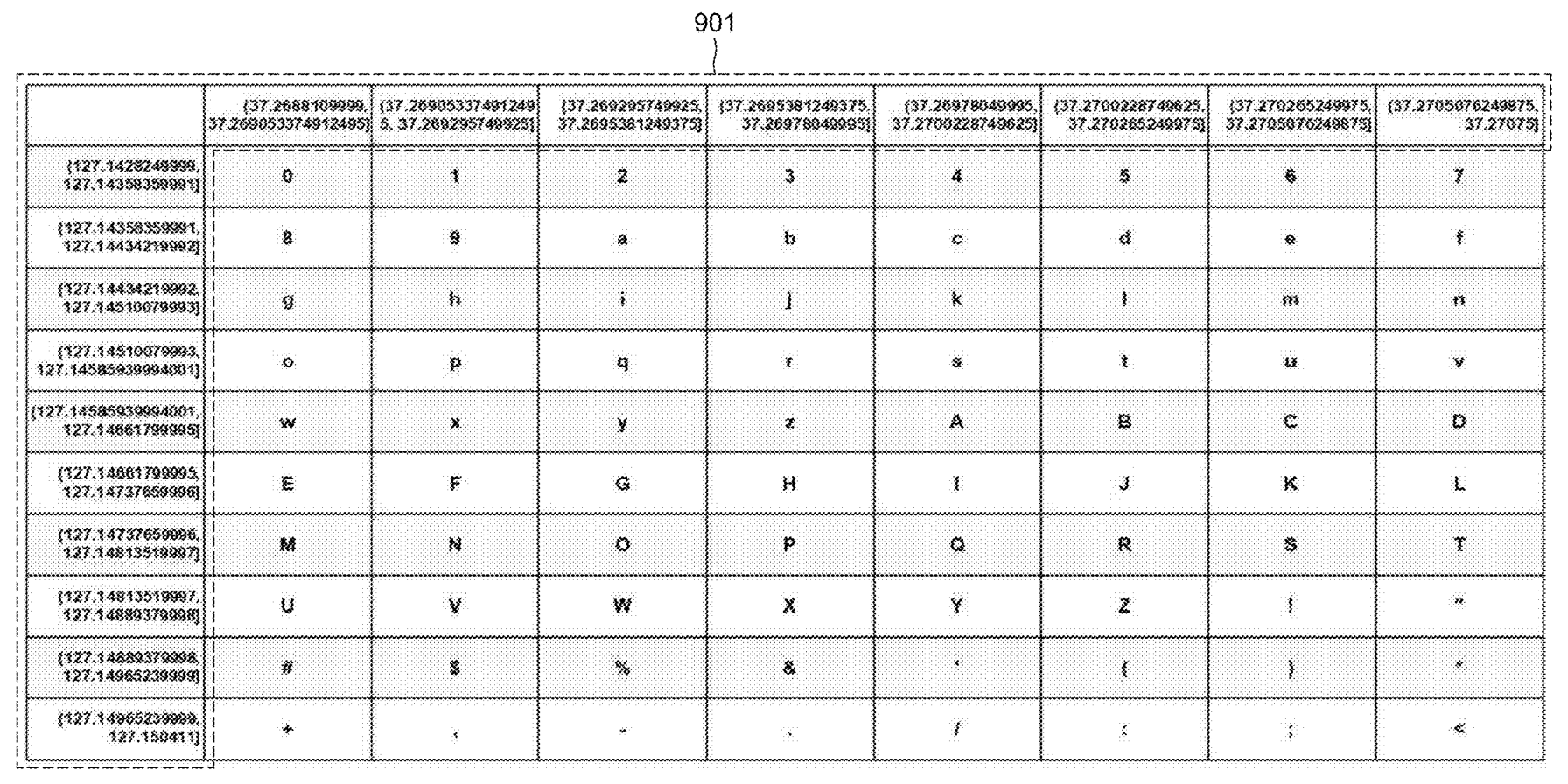

More specifically, with reference to FIG. 9, the server 200 for providing whether the patient is accompanied by the caregiver may provide the ASCII code to each of the zones in the drawing. In this case, the server 200 for providing whether the patient is accompanied by the caregiver may set a logical zone 901 on the basis of the actual drawing. In this case, the server 200 for providing whether the patient is accompanied by the caregiver may provide the inherent identification character for each zone to the preset logical zone 901.

With reference back to FIG. 8C, the server 200 for providing whether the patient is accompanied by the caregiver may match the positions of the dangerous situation target and the caregiver and the zone. In this case, the server 200 for providing whether the patient is accompanied by the caregiver may further include data related to floors.

Figure 10:
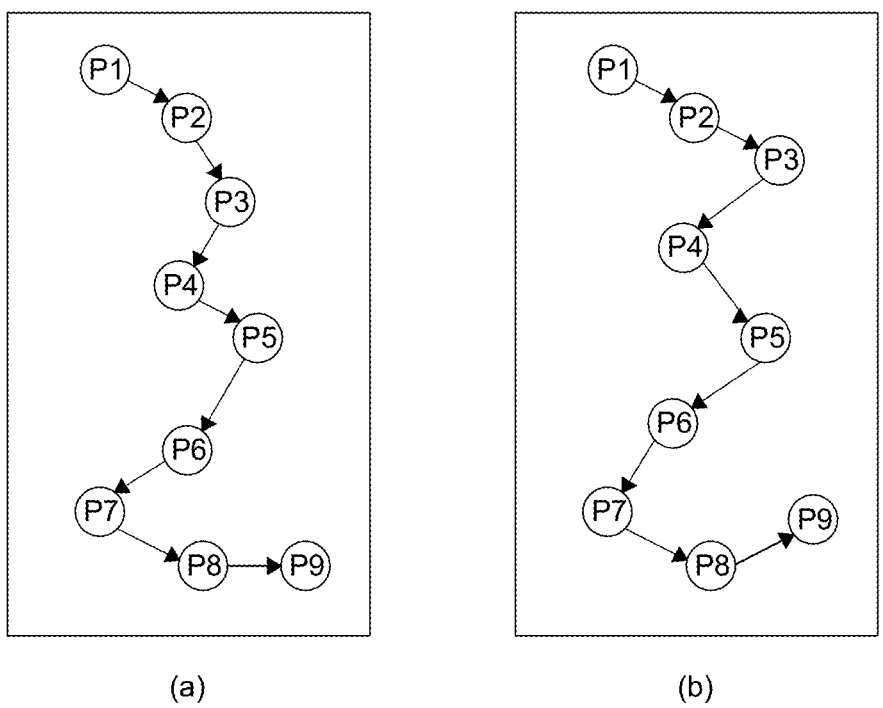

More specifically, with reference to FIG. 10, (a) may indicate the position history of the risk target, and (b) may indicate the position history of the caregiver. In this case, the server 200 for providing whether the patient is accompanied by the caregiver may collect the RTLS data of the risk target and the caregiver. In this case, the server 200 for providing whether the patient is accompanied by the caregiver may perform zone mapping on the RTLS data of the risk target and the caregiver. In addition, the server 200 for providing whether the patient is accompanied by the caregiver may generate the ASCII code and floor data corresponding to the RTLS data of the risk target and the caregiver. In this case, the server 200 for providing whether the patient is accompanied by the caregiver may generate time-sequence movement zone data of the risk target and the caregiver. For example, in case that the risk target moves from first floor A to first floor B and from first floor B to first floor A, 1FA, 1FB, and 1FA may be generated. In this case, the floor data related to a first basement may be generated as B1F, and the floor data related to ground floors may be generated as number+F.

In this case, the server 200 for providing whether the patient is accompanied by the caregiver may remove repeated movement zone data. In this case, the repeated movement zone data may be data in which the zone remains in place without moving. For example, in case that the data are generated as 1FA, 1FB, 1FB, and 1FC, the data may be realigned as 1FA, 1FB, and 1FC.

With reference back to FIG. 5, the server 200 for providing whether the patient is accompanied by the caregiver performs a process of determining whether the patient is accompanied by the caregiver on the basis of the position for each caregiver (S511). In this case, the server 200 for providing whether the patient is accompanied by the caregiver may perform the process of determining whether the patient is accompanied by the caregiver on the basis of a Levenshtein distance. In this case, the server 200 for providing whether the patient is accompanied by the caregiver may determine whether the patient is accompanied by the caregiver by converting the Levenshtein distance into a percentile.

More specifically, with reference to FIG. 11, the server 200 for providing whether the patient is accompanied by the caregiver may extract an actual position in the drawing by covering the actual position into the logical zone. In this case, the server 200 for providing whether the patient is accompanied by the caregiver may determine whether the patient is accompanied by the caregiver by means of a similarity calculation method on the basis of a position character string for each extracted target. In this case, the similarity may mean the number of cases of insertion/removal/substitution required for one character string to become another character string. For example, in case that the movement zone data of the risk target are 1FA, 1FB, and 1FA and the movement zone data of the caregiver are 1FA, 1FB, and 1FC, the distance value may be 1 because 1FA, which is the last character strings of risk target, only needs to be substituted with 1FC.

With reference to FIG. 11A, a character string 1101 of the risk target may be SELECT, and a character string 1102 of the caregiver may be SELECTION. In this case, the distance value may be 3 because ION only needs to be inserted to change SELECT to SELECTION.

With reference to FIG. 11B, the server 200 for providing whether the patient is accompanied by the caregiver may convert the Levenshtein distance into a percentile by using the following expression. In this case, the server 200 for providing whether the patient is accompanied by the caregiver may calculate the percentile on the basis of a numerical value having a longer character string of the risk target or the caregiver. In this case, the server 200 for providing whether the patient is accompanied by the caregiver may calculate the percentile on the basis of (numerical value of long character string–distance value/numerical value of long character string). For example, the calculation may be performed on the basis of the expression of (9−3/9*100). In this case, in case that the percentile numerical value is equal to or more than a critical value, the server 200 for providing whether the patient is accompanied by the caregiver may determine that the risk target is accompanied by the caregiver.

As described above, the server 200 for providing whether the patient is accompanied by the caregiver may utilize the proximity calculation method performed in consideration of a time difference between position signals collected from the devices of the patient and the caregiver and prevent an error that occurs at the time of simply calculating a distance of the position data of the patient and the caregiver. Therefore, it is possible to improve the precision of the process of identifying whether the patient is accompanied by the caregiver. With reference back to FIG. 5, the server 200 for providing whether the patient is accompanied by the caregiver determines whether the patient is accompanied by the caregiver for each of the caregivers (S512). In this case, in case that the server 200 determines that whether the risk target is accompanied by the caregiver is an accompanied state, the server 200 for providing whether the patient is accompanied by the caregiver ends the process of determining whether the patient is accompanied by the caregiver (S514). In this case, in case that the server 200 determines that whether the risk target is accompanied by the caregiver is a non-accompanied state, the server 200 for providing whether the patient is accompanied by the caregiver determines whether whether the patient is accompanied by all the caregivers is checked (S513). In this case, in case that it is ascertained that the patient is accompanied only by some of the caregivers instead of all the caregivers, caregiver data different from the caregiver is selected, and the process goes to step 510.

Next, in case that the server 200 ascertains that the patient is accompanied by all the caregivers, the server 200 for providing whether the patient is accompanied by the caregiver designates the risk target to a lone wandering risk person (S515).

Next, the server 200 for providing whether the patient is accompanied by the caregiver initiates a lone wandering dangerous situation notification related to the lone wandering risk person (S516). In this case, the server 200 for providing whether the patient is accompanied by the caregiver may generate data related to the lone wandering risk person. For example, with reference to FIG. 11C, the data related to the lone wandering risk person may be generated as Gil-dong Hong, H1, fall risk zone 1, A1, and lone wandering=Y. In this case, the server 200 for providing whether the patient is accompanied by the caregiver queries information on the caregiver designated to the lone wandering risk person. In this case, the server 200 for providing whether the patient is accompanied by the caregiver may generate notification generation data to be transferred to the queried caregiver. Further, the server 200 for providing whether the patient is accompanied by the caregiver may transfer the notification to the caregiver. In another embodiment, the server 200 for providing whether the patient is accompanied by the caregiver may provide the user device 100 with the data related to the lone wandering risk person.

As described above, the server 200 for providing whether the patient is accompanied by the caregiver may identify whether the patient is accompanied by the caregiver and generate an alarm to the caregiver on the basis of the identification result. Therefore, it is possible to prevent a safety accident that may occur when the patient wanders alone.

Although the embodiments of the present disclosure have been described in detail with reference to the accompanying drawings, the present disclosure is not limited thereto and may be embodied in many different forms without departing from the technical concept of the present disclosure. Therefore, the embodiments disclosed in the present disclosure are provided for illustrative purposes only but not intended to limit the technical spirit of the present disclosure. The scope of the technical spirit of the present disclosure is not limited thereby. Therefore, it should be understood that the above-described embodiments are illustrative in all aspects and do not limit the present disclosure. The protective scope of the present disclosure should be construed based on the following claims, and all the technical spirit in the equivalent scope thereto should be construed as falling within the scope of the present disclosure.

What is claimed is:

1. A method for ascertaining whether a patient is accompanied by a caregiver, the method being implemented by a processor of a server and comprising:
    receiving position data of the patient and position data of the caregiver;
    determining whether the patient is accompanied by the caregiver based on the position data of the patient and the position data of the caregiver;
    generating a risk alarm related to the patient based on the determining whether the patient is accompanied by the caregiver; and
    transmitting the risk alarm from the server to a user device,
    wherein the determining whether the patient is accompanied by the caregiver includes a proximity calculation performed with reference to a time difference between collecting the patient position data and collecting the caregiver position data,
    the method further comprising:
        mapping real-time position locating system (RTLS) data related to the patient and the caregiver based on an ASCII code,
        wherein the RTLS data is mapped before it is determined whether the patient is accompanied by the caregiver.

2. The method of claim 1, further comprising:
    setting a danger zone related to the patient,
    wherein the danger zone is set before the patient position data and the caregiver position data are received from a position transmitter of the patient and a position transmitter of the caregiver, respectively.

3. The method of claim 2, wherein the danger zone includes at least one zone in which a probability of a fall accident of the patient is greater than or equal to a first critical value.

4. The method of claim 2, further comprising:
    determining whether the patient is positioned in the danger zone based on the patient position data,
    wherein the patient position relative to the danger zone is determined before it is determined whether the patient is accompanied by the caregiver.

5. The method of claim 4, further comprising:
    setting a danger time related to the patient,
    wherein the danger time includes at least one time period and is set before the patient position data and the caregiver position data are received from the position transmitter of the patient and the position transmitter of the caregiver, respectively.

6. The method of claim 5, further comprising:
    determining, based on a current time, whether the danger time applies to the patient when it is determined that the patient is positioned in the danger zone.

7. The method of claim 1, wherein the RTLS data mapping includes removing repetitious ASCII code appearing in the patient position data or the caregiver position data.

8. The method of claim 1,
    wherein the proximity calculation includes converting over time a route of the patient and a route of the caregiver into character strings, respectively, based on a logical zone, and
    wherein the determining whether the patient is accompanied by the caregiver is based on a length difference between the character string of the patient and the character string of the caregiver.

9. A device for ascertaining whether a patient is accompanied by a caregiver, the device being implemented by a server comprising:
    a communication part;
    a storage part; and
    a processor operably connected to the communication part and the storage part and configured to
        receive position data of the patient and position data of the caregiver,
        determine whether the patient is accompanied by the caregiver based the position data of the patient and the position data of the caregiver,
        generate a risk alarm related to the patient based on the determining whether the patient is accompanied by the caregiver, and
        transmit the risk alarm from the server to a user device, wherein the processor determines whether the patient is accompanied by the caregiver by a proximity calculation performed with reference to a time difference between collecting the patient position data and collecting the caregiver position data, wherein the processor is further configured to map real-time position locating system (RTLS) data related to the patient and the caregiver based on an ASCII code, and wherein the RTLS data is mapped before it is determined whether the patient is accompanied by the caregiver.

10. The device of claim 9, wherein the processor is further configured to set a danger zone related to the patient, and wherein the danger zone is set before the patient position data and the caregiver position data are received from a position transmitter of the patient and a position transmitter of the caregiver, respectively.

11. The device of claim 10, wherein the danger zone includes at least one zone in which a probability of a fall accident of the patient is greater than or equal to a first critical value.

12. The device of claim 10, wherein the processor is further configured to determine whether the patient is positioned in the danger zone based on the patient position data, and wherein the patient position relative to the danger zone is determined before it is determined whether the patient is accompanied by the caregiver.

13. The device of claim 12, wherein the processor is further configured to set a danger time related to the patient, and wherein the danger time includes at least one time period and is set before the patient position data and the caregiver position data are received from the position transmitter of the patient and the position transmitter of the caregiver, respectively.

14. The device of claim 13, wherein the processor is further configured to determine, based on a current time, whether the danger time applies to the patient when it is determined that the patient is positioned in the danger zone.

15. The device of claim 9, wherein the RTLS data mapping includes removing repetitious ASCII code appearing in the patient position data or the caregiver position data.

16. The device of claim 7, wherein the proximity calculation includes converting over time a route of the patient and a route of the caregiver into character strings, respectively, based on a logical zone, and wherein the determining whether the patient is accompanied by the caregiver is based on a length difference between the character string of the patient and the character string of the caregiver.

* * * * *